United States Patent [19]
Birglechner

[11] Patent Number: 5,996,864
[45] Date of Patent: *Dec. 7, 1999

[54] HOLDER FOR TOOTH TREATMENT MATERIAL AND METHOD

[75] Inventor: Werner Birglechner, Konstanz, Germany

[73] Assignee: Dentsply DeTrey GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/825,858

[22] Filed: Apr. 2, 1997

[51] Int. Cl.⁶ .................................................... A61C 19/00
[52] U.S. Cl. ........................................... 224/217; 433/163
[58] Field of Search ..................... 224/217, 218; 433/49, 163; D7/558, 586, 396.2, 396.6, 401.1

[56] References Cited

U.S. PATENT DOCUMENTS

| | | | |
|---|---|---|---|
| 386,750 | 7/1888 | Kimball | 433/49 |
| 667,083 | 1/1901 | Goldsmith | 224/217 |
| 2,140,231 | 12/1938 | Jefferies | 215/12 |
| 2,356,722 | 8/1944 | Harris | 224/217 X |
| 2,865,384 | 12/1958 | Noon | 132/73 |
| 2,970,379 | 2/1961 | Hardgrove | 433/163 |
| 3,327,391 | 6/1967 | Malm | |
| 3,416,542 | 12/1968 | Shook | 132/73 |
| 3,485,353 | 12/1969 | Reiter | 206/63.5 |
| 4,646,953 | 3/1987 | Marshall et al. | 224/217 |
| 4,717,057 | 1/1988 | Porteous | 224/217 |
| 4,844,308 | 7/1989 | Porteous | 224/217 |
| 4,988,296 | 1/1991 | Spencer | 433/163 |
| 5,016,795 | 5/1991 | Porteous | 224/217 |
| 5,048,731 | 9/1991 | Moreschini | 43/163 |
| 5,169,315 | 12/1992 | Bull | 433/163 |
| 5,368,482 | 11/1994 | Johnsen et al. | 433/163 |

FOREIGN PATENT DOCUMENTS 677 258  10/1995  European Pat. Off. .

*Primary Examiner*—Renee S. Luebke
*Attorney, Agent, or Firm*—Dale R. Lovercheck; James B. Bieber

[57] ABSTRACT

The invention provides a tooth polishing paste holder having a cup member, a connector member and a base member. The cup has an inner wall. The inner wall has a circumference less than 10 cm. The connector connects the cup to the base. The base is adapted to support the cup in an upright position on a horizontal surface.

21 Claims, 1 Drawing Sheet

HOLDER FOR TOOTH TREATMENT MATERIAL AND METHOD

The invention relates to holders for tooth treatment material. The invention provides a holder for tooth treatment material, such as polishing paste, the holder having a cup, a connector and a base adapted to support the cup in an upright position on a horizontal surface.

BACKGROUND OF THE INVENTION

The prior art uses metal rings and plastic fingerclips to hold polishing paste in a single use container. For example NUPRO (trademark) dental polishing paste is sold by Dentsply International Inc in a single use container. One prior art clip holds the container to a finger of a dentist (or hygienist) while the single use container is fixed on top of the clip.

Prior art fingerclip holders are able to clasp single use containers, but are not adapted to hold paste without a container. A prior art fingerclip, while in use is held firmly to the finger which presses on the finger becoming uncomfortable after a while. Sharp edges of the metal clips damage the user's examination glove(s). Prior art holder mounting and removal require the use of a second hand to move the holder from or to the user's finger. Thus, a prior art holder fingerclip cannot be removed from the user's finger by the hand on which the holder is mounted, so a second hand is needed. Prior art holders bend and loosen the hold on the container when removing polishing paste from the container. Retention for paste containers in prior art holders is therefore poor and decreases over time.

SUMMARY OF THE INVENTION

Holders in accordance with the invention provide the user with the ability to hold all kinds of dental materials and medicaments like polishing paste in cups, in bulk, fluoride varnish and gel and other materials for professional use. Holders in accordance with the invention make it easy to directly apply material into the patient's mouth. Holders in accordance with the invention provide users with the ability to hold a holder and a dental instrument or a dental tool at the same time in one hand without any discomfort or interference by the dental tool or instrument in the use of the holder.

Holders in accordance with the invention are made of autoclavable material. Holders in accordance with the invention have no wear or breakage of the clips by time. Holders in accordance with the invention are used in one hand with no need for a second hand to remove the holder from and/or clip the holder to the finger. Holders in accordance with the invention are easy to pick-up and put down on a tray. Holders in accordance with the invention provides the user with the ability to be used between the fingers of your choice either on right or left hand in upright or downside position.

Holders in accordance with the invention provide users with the ability to be put down at the tray in upright position. Holders in accordance with the invention allow different grasps of a holder to accommodate hand positions.

Tooth polishing paste is typically effectively a nonvolatile material containing abrasive particles, and is applied to teeth in a patient's mouth while supported by a motor driven rotating carrier.

The prior art does not provide a tooth polishing paste holder having a cup member, a connector member and a base member wherein the cup has an inner wall with a circumference less than 10 cm, the connector connects the cup to the base and the base is adapted to support the cup in an upright position on a horizontal surface.

It is an object of the invention to provide an undivided unitary tooth polishing paste holder having a cup member, a connector member and a base member wherein the cup has an inner wall with a circumference less than 10 cm, the connector connects the cup to the base and the base is adapted to support the cup in an upright position on a horizontal surface.

DETAILED DESCRIPTION OF THE INVENTION

Figure 1:
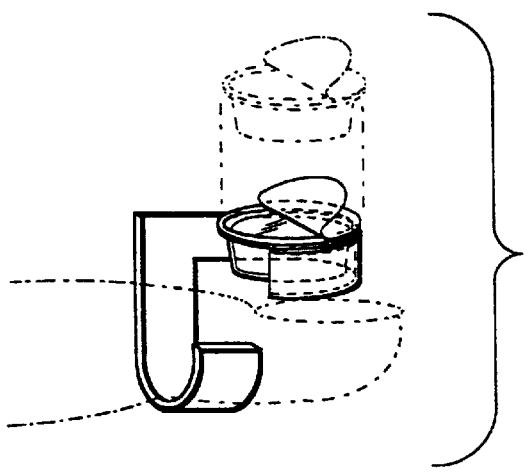
FIG. 1 is an illustration of a prior art paste holder.
Figure 3:
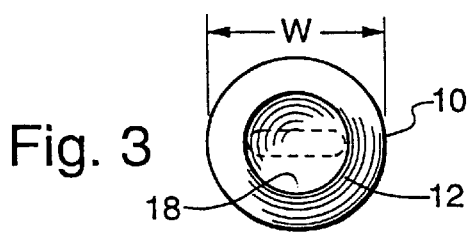
FIG. 3 is a top view of the holder shown in FIGS. 2–6.
Figure 2:
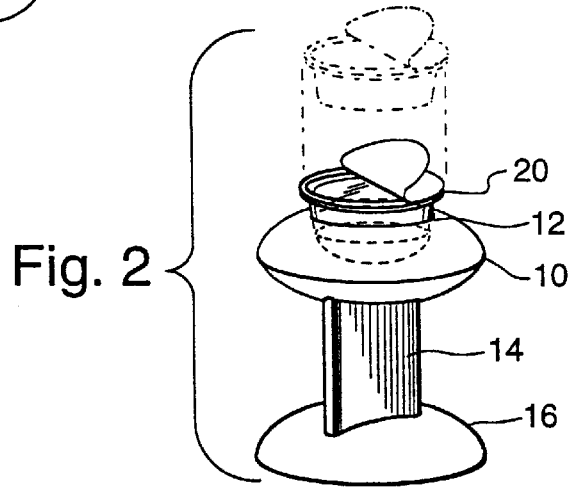
FIG. 2 is a perspective view of a holder in accordance with the invention.
Figure 4:
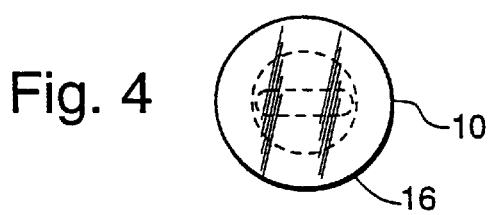
FIG. 4 is a bottom view of the holder shown in FIGS. 2–6.
Figure 5:
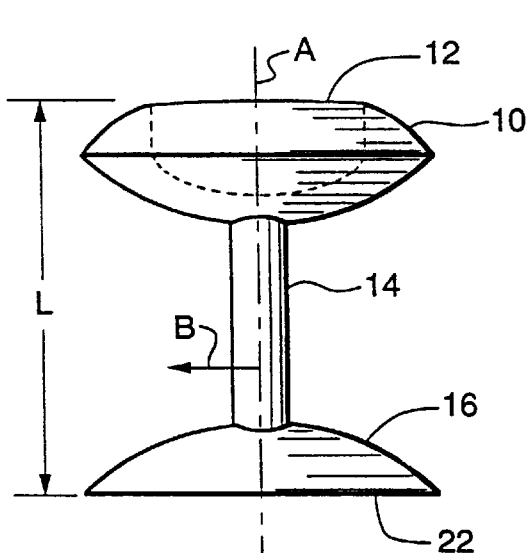
FIGS. 5 and 6 are enlarged side elevational views taken at right angles to each other of the holder shown in FIGS. 2–6.
Figure 6:
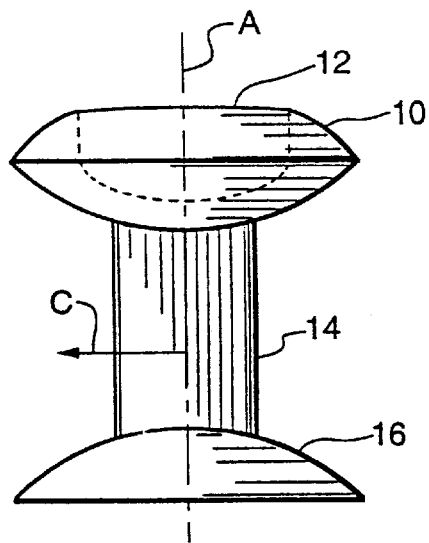

The invention is now described with more particular reference to FIGS. 2 through 6. The invention provides a tooth polishing paste holder 10, having a cup member 12, a connector member 14 and a base member 16. The cup 12 has an inner wall 18. The inner wall 18 has a circumference less than 10 cm. Preferably, the inner wall 18 has a circumference less than 6 cm. The connector 14 connects the cup 12 to the base 16.

The base 16 is adapted to support the cup 12 in an upright position on a horizontal surface. The connector 14 is substantially rectangular in cross-section. The holder 10 is made of a material adapted to not melt and maintain the shape of the holder at temperatures greater than 100° C. The connector 14 has a length to width ratio between 1 to 1 and 4 to 1, and a width to depth ratio between 2 to 1 and 30 to 1. Preferably, the connector 14 has a length to width ratio between 1 to 1 and 3 to 1, and a width to depth ratio between 2 to 1 and 10 to 1. Holder 10 is preferably used in combination with a container 20 which supports tooth polishing paste therein while the container is supported by the cup 12.

Holder 10 is preferably used in combination with tooth polishing paste while the paste is supported by the cup 12. Preferably the inner wall 18 has a circumference less than 5 cm. Preferably the paste comprises fine particles of abrasive material.

Preferably cup 12 has a truncated rounded upper face and truncated rounded lower face, and said base has a truncated rounded upper face and a planar lower face.

Holder 10 has a central axis A which extends vertically while the lower face 22 of the base 16 is positioned in a horizontal plane, for example by being substantially coplanar with and supported by a horizontal surface. The connector 14 extends laterally from the vertical axis in two orthogonal directions B and C. Preferably the connector extends laterally more than twice as far in one orthogonal direction C than in the other orthogonal direction B. More preferably the connector extends laterally more than thrice as far in one orthogonal direction C than in the other orthogonal direction B. Most preferably the connector extends laterally more than four times further in one orthogonal direction C than in the other orthogonal direction B.

The invention provides a method of dispensing tooth polishing paste by providing a paste holder having a cup, a connector and a base, the connector connecting the cup to the base, the base being adapted to support the cup in an upright position on a horizontal surface, the cup supporting tooth polishing paste, and dispensing the tooth polishing paste from the cup. The user positions a container in the cup. The container supports dental treatment material such as tooth polishing paste. Alternatively the user positions dental treatment material such as tooth polishing paste in the cup. Conveniently the user positions the connector between two fingers of one of the user's hands. Then the user applies the paste either to a hand held dental tool or hand held dental device or to a tooth polishing device for polishing one or more teeth in a patient's mouth. Preferably the paste comprises fine particles of abrasive material.

Preferably the tooth polishing paste holder 10 has an overall length (L) which is less than 5 cm and more than 0.5 cm, and cup 12 has a width (W) which is less than 5 cm and more than 0.5 cm. More preferably the tooth polishing paste holder (L) has an overall length (L) which is less than 4 cm and more than 1 cm, and cup 12 has a width (W) which is less than 5 cm and more than 1 cm.

Preferably holder 10 is made of material having a melting point higher than 100° C. and is effectively insoluble in acetone at 23° C.

Preferably holder 10 is held by positioning the connector between two adjacent fingers of a user's hand, and released by the user spreading those fingers.

It should of course be understood that this invention may be modified in various aspects. Such modifications all are within the scope of the claims which follow.

What is claims is:

1. An undivided unitary holder for tooth treatment material comprising:
   a cup,
   a connector and
   a base,
   said connector being undivided from, unitary with and integrally connected to both said cup and said base,
   said cup having an inner wall, said inner wall having a circumference less than 10 cm,
   said cup, connector and base being positioned along and intersected by a central axis,
   said connector being substantially rectangular extending laterally from said central axis in a first and a second direction, said connector extending laterally more than twice as far in said first direction than in said second direction, said first direction being orthogonal to said second direction,
   said base being adapted to support the cup in an upright position on a horizontal surface, said connector having a length, a width and a depth, said length being longer than said width or depth, said connector length extending along said central axis,
   said base having a circular planar lower face, and said base extending substantially laterally from said connector.

2. The holder of claim 1 wherein said holder is made of a material adapted to not melt and maintain the shape of the holder at temperatures greater than 100° C.

3. The holder of claim 1 wherein said connector has a length to width ratio between 1 to 1 and 4 to 1, and a width to depth ratio between 2 to 1 and 30 to 1.

4. The holder of claim 1 wherein said connector has a length to width ratio between 1 to 1 and 3 to 1, and a width to depth ratio between 2 to 1 and 10 to 1.

5. The holder of claim 1 in combination with a container supporting tooth polishing paste said container being supported by said cup.

6. The holder of claim 1 in combination with tooth polishing paste said paste being supported by said cup.

7. The holder of claim 1 wherein said inner wall has a circumference less than 6 cm.

8. The holder of claim 1 wherein said cup has a truncated rounded upper face and a truncated rounded lower face, and said base has a truncated rounded upper face and a planar lower face.

9. The holder of claim 1 wherein said connector has a length to width ratio between 1 to 1 and 3 to 1.

10. The holder of claim 1 wherein said base has a rounded upper face.

11. The holder of claim 1 wherein said holder has an overall length which is less than 5 cm and more than 0.5 cm, and said cup has a width which is less than 5 cm and more than 0.5 cm.

12. The holder of claim 1 wherein said holder has an overall length which is less than 4 cm and more than 1 cm, and said cup has a width which is less than 5 cm and more than 1 cm.

13. A method of dispensing tooth polishing paste comprising:
   providing tooth polishing paste supported by an undivided unitary paste holder having a cup, a connector and a base having a lower face, said connector being substantially rectangular, said connector being undivided from, unitary with and integrally connected to both said cup and said base, said base having a circular planar lower face, said base extending substantially laterally in all directions from said connector and being adapted to support the cup in an upright position on a horizontal surface, said cup supporting said tooth polishing paste,
   positioning said connector between two adjacent fingers of a user's hand,
   dispensing said tooth polishing paste from said cup, and releasing said holder by spreading said fingers, while positioning said holder in an upright position with said lower face of said base supported by and coplanar with a horizontal surface.

14. The method of claim 13 further comprising providing a container and positioning said container in said cup, and wherein said tooth polishing paste is supported in said container.

15. The method of claim 13 further comprising positioning tooth polishing paste in said cup.

16. The method of claim 13 further comprising applying said paste to a tooth polishing device for polishing one or more teeth in a patient's mouth.

17. A method of dispensing tooth polishing paste comprising:
   providing tooth polishing paste supported by an undivided unitary paste holder having a cup, a connector and a base having a lower face, said connector being substantially rectangular, said connector being undivided from, unitary with and integrally connected to both said cup and said base, said base having a circular planar lower face, said base extending substantially laterally in all directions from said connector and being adapted to support the cup in an upright position on a horizontal surface, said cup supporting said tooth polishing paste,
   positioning said connector between two adjacent fingers of a user's hand, dispensing said tooth polishing paste from said cup, and positioning said holder in an upright position with said lower face of said base supported by and coplanar with a horizontal surface.

18. The method of claim 17 further comprising providing a container and positioning said container in said cup, and wherein said tooth polishing paste is supported in said container.

19. The method of claim 17 further comprising applying said paste to a tooth polishing device for polishing one or more teeth in a patient's mouth.

20. The method of claim 17 wherein said paste comprises fine particles of abrasive material.

21. The method of claim 17 wherein said holder comprises material having a melting point higher than 100° C. and said material is effectively insoluble in acetone at 23° C.

* * * * *